(12) United States Patent
Rosenberg et al.

(10) Patent No.: US 8,636,776 B2
(45) Date of Patent: *Jan. 28, 2014

(54) SPINAL ROD APPROXIMATOR

(75) Inventors: William S. Rosenberg, Overland Park, KS (US); Thomas V. Doherty, Hesperia, CA (US); Mark C. Boomer, Phoenix, AZ (US); Bryan S. Jones, West Roxbury, MA (US)

(73) Assignee: DePuy Spine, Inc., Raynham, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 13/032,247

(22) Filed: Feb. 22, 2011

(65) Prior Publication Data
US 2011/0144695 A1 Jun. 16, 2011

Related U.S. Application Data

(63) Continuation of application No. 10/352,687, filed on Jan. 28, 2003, now Pat. No. 7,988,698.

(51) Int. Cl.
*A61B 17/70* (2006.01)

(52) U.S. Cl.
USPC .......................................................... 606/270

(58) Field of Classification Search
USPC ......... 606/246, 250, 260, 264, 265, 267, 270, 606/99
See application file for complete search history.

(56) References Cited

U.S. PATENT DOCUMENTS

| | | |
|---|---|---|
| 410,780 A | 9/1889 | Cahn |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Frederick |
| 2,248,054 A | 7/1941 | Becker |
| 2,248,057 A | 7/1941 | Bond |
| 2,291,413 A | 7/1942 | Siebrandt |

(Continued)

FOREIGN PATENT DOCUMENTS

| | | |
|---|---|---|
| DE | 4238339 A1 | 5/1994 |
| DE | 29806563 U1 | 6/1998 |

(Continued)

OTHER PUBLICATIONS

Extended European Search Report issued Apr. 26, 2012 for Application No. 08781067.7 (7 Pages).

(Continued)

*Primary Examiner* — Anu Ramana
(74) *Attorney, Agent, or Firm* — Nutter McClennen & Fish LLP

(57) ABSTRACT

Spinal implants, spinal rod approximators for seating a stabilizing rod in a rod-receiving portion of a spinal implant, and methods for using the same are provided. In one embodiment, a spinal rod approximator is provided including an elongate member having a grasping member formed on a distal end thereof, and a rod pusher member slidably mated to or mounted on the elongate member. The grasping member is effective to grasp a portion of a spinal implant, and the pusher member is effective to grasp and engage a stabilizing rod and push the rod into a rod-receiving portion of the spinal implant being grasped by the grasping member.

15 Claims, 12 Drawing Sheets

(56) References Cited

U.S. PATENT DOCUMENTS

| | | |
|---|---|---|
| 2,370,407 A | 2/1945 | McCartney |
| 2,800,820 A | 7/1957 | Retterath |
| 3,960,147 A | 6/1976 | Murray |
| 4,237,875 A | 12/1980 | Termanini |
| 4,271,836 A | 6/1981 | Bacal et al. |
| 4,411,259 A | 10/1983 | Drummond |
| 4,445,513 A | 5/1984 | Ulrich et al. |
| 4,655,223 A | 4/1987 | Kim |
| 4,809,695 A | 3/1989 | Gwathmey et al. |
| 4,896,661 A | 1/1990 | Bogert et al. |
| 5,014,407 A | 5/1991 | Boughten et al. |
| 5,020,519 A | 6/1991 | Hayes et al. |
| D346,217 S | 4/1994 | Sparker et al. |
| 5,306,248 A | 4/1994 | Barrington |
| 5,364,397 A | 11/1994 | Hayes et al. |
| 5,391,170 A | 2/1995 | McGuire et al. |
| 5,429,641 A | 7/1995 | Gotfried et al. |
| 5,431,658 A | 7/1995 | Moskovich |
| 5,484,440 A | 1/1996 | Allard |
| 5,545,165 A | 8/1996 | Biedermann et al. |
| 5,551,320 A | 9/1996 | Horobec et al. |
| 5,616,143 A | 4/1997 | Schlapfer et al. |
| 5,649,931 A | 7/1997 | Bryant et al. |
| 5,672,175 A | 9/1997 | Martin |
| 5,683,399 A | 11/1997 | Jones |
| 5,697,933 A | 12/1997 | Gundlapalli et al. |
| 5,707,371 A | 1/1998 | Metz-Stavenhagen et al. |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,810,878 A | 9/1998 | Burel et al. |
| 5,910,141 A | 6/1999 | Morrison et al. |
| 5,941,885 A | 8/1999 | Jackson |
| 5,951,564 A | 9/1999 | Schroder et al. |
| 5,951,579 A | 9/1999 | Dykes |
| 6,010,509 A | 1/2000 | Delgado et al. |
| 6,036,692 A | 3/2000 | Burel et al. |
| 6,099,528 A | 8/2000 | Saurat et al. |
| 6,123,707 A | 9/2000 | Wagner |
| 6,139,549 A | 10/2000 | Keller |
| 6,183,472 B1 | 2/2001 | Lutz |
| 6,210,330 B1 | 4/2001 | Tepper et al. |
| 6,251,112 B1 | 6/2001 | Jackson |
| 6,258,090 B1 | 7/2001 | Jackson |
| 6,371,973 B1 | 4/2002 | Tepper et al. |
| 6,440,133 B1 | 8/2002 | Beale et al. |
| 6,440,142 B1 | 8/2002 | Ralph et al. |
| 6,440,144 B1 | 8/2002 | Bacher |
| 6,511,484 B2 | 1/2003 | Torode et al. |
| 6,530,929 B1 | 3/2003 | Justis et al. |
| 6,589,249 B2 | 7/2003 | Sater et al. |
| 6,648,888 B1 | 11/2003 | Shluzas |
| 6,660,006 B2 | 12/2003 | Markworth et al. |
| 6,726,692 B2 | 4/2004 | Bette et al. |
| 6,743,231 B1 | 6/2004 | Gray et al. |
| 6,746,449 B2 | 6/2004 | Jones et al. |
| 6,752,832 B2 | 6/2004 | Neumann |
| 6,755,829 B1 | 6/2004 | Bono et al. |
| 6,790,208 B2 | 9/2004 | Oribe et al. |
| 6,790,209 B2 | 9/2004 | Beale et al. |
| 6,827,722 B1 | 12/2004 | Schoenefeld |
| 7,081,117 B2 * | 7/2006 | Bono et al. .............. 606/300 |
| 7,083,621 B2 | 8/2006 | Shaolian et al. |
| 7,156,849 B2 | 1/2007 | Dunbar et al. |
| 7,179,254 B2 | 2/2007 | Pendekanti et al. |
| 7,179,261 B2 | 2/2007 | Sicvol et al. |
| 7,278,995 B2 | 10/2007 | Nichols et al. |
| 7,320,689 B2 | 1/2008 | Keller |
| 7,371,239 B2 | 5/2008 | Dec et al. |
| 7,462,182 B2 | 12/2008 | Lim |
| 7,485,120 B2 | 2/2009 | Ray |
| 7,491,207 B2 | 2/2009 | Keyer et al. |
| 7,527,638 B2 | 5/2009 | Anderson et al. |
| 7,572,281 B2 | 8/2009 | Runco et al. |
| 7,621,918 B2 | 11/2009 | Jackson |
| 7,651,502 B2 | 1/2010 | Jackson |
| 7,666,188 B2 | 2/2010 | Anderson et al. |
| 7,708,763 B2 | 5/2010 | Selover et al. |
| 7,867,237 B2 | 1/2011 | Stad et al. |
| 7,887,541 B2 | 2/2011 | Runco et al. |
| 7,988,698 B2 | 8/2011 | Rosenberg et al. |
| 8,172,847 B2 | 5/2012 | Dziedzic et al. |
| 2002/0072752 A1 | 6/2002 | Zucherman et al. |
| 2002/0095153 A1 | 7/2002 | Jones et al. |
| 2003/0009168 A1 | 1/2003 | Beale et al. |
| 2003/0028195 A1 | 2/2003 | Bette |
| 2003/0083747 A1 | 5/2003 | Winterbottom et al. |
| 2001/0029376 A1 | 7/2003 | Sater et al. |
| 2003/0125750 A1 | 7/2003 | Zwirnmann et al. |
| 2003/0149438 A1 | 8/2003 | Nichols et al. |
| 2003/0171756 A1 | 9/2003 | Fallin et al. |
| 2003/0191370 A1 | 10/2003 | Phillips |
| 2003/0199872 A1 | 10/2003 | Markworth et al. |
| 2003/0225408 A1 | 12/2003 | Nichols et al. |
| 2004/0049191 A1 | 3/2004 | Markworth et al. |
| 2004/0147936 A1 | 7/2004 | Rosenberg et al. |
| 2004/0147937 A1 | 7/2004 | Dunbar et al. |
| 2004/0172057 A1 | 9/2004 | Guillebon et al. |
| 2004/0176779 A1 | 9/2004 | Casutt et al. |
| 2004/0220567 A1 | 11/2004 | Eisermann et al. |
| 2004/0254576 A1 | 12/2004 | Dunbar et al. |
| 2004/0267275 A1 | 12/2004 | Cournoyer et al. |
| 2005/0015094 A1 | 1/2005 | Keller |
| 2005/0015095 A1 | 1/2005 | Keller |
| 2005/0033299 A1 | 2/2005 | Shluzas |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0143749 A1 | 6/2005 | Zalenski et al. |
| 2005/0149036 A1 | 7/2005 | Varieur et al. |
| 2005/0149048 A1 | 7/2005 | Leport et al. |
| 2005/0149053 A1 | 7/2005 | Varieur et al. |
| 2005/0192570 A1 | 9/2005 | Jackson |
| 2005/0192579 A1 | 9/2005 | Jackson |
| 2005/0228392 A1 | 10/2005 | Keyer et al. |
| 2005/0261702 A1 | 11/2005 | Oribe et al. |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036260 A1 | 2/2006 | Runco et al. |
| 2006/0069391 A1 | 3/2006 | Jackson |
| 2006/0074418 A1 | 4/2006 | Jackson |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0166534 A1 | 7/2006 | Brumfield et al. |
| 2006/0166535 A1 | 7/2006 | Brumfield et al. |
| 2006/0293692 A1 | 12/2006 | Whipple et al. |
| 2007/0093849 A1 | 4/2007 | Jones et al. |
| 2007/0100347 A1 | 5/2007 | Stad et al. |
| 2007/0129731 A1 | 6/2007 | Sicvol et al. |
| 2007/0161998 A1 | 7/2007 | Whipple |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0213722 A1 | 9/2007 | Jones et al. |
| 2007/0233097 A1 | 10/2007 | Anderson et al. |
| 2007/0260261 A1 | 11/2007 | Runco et al. |
| 2007/0270880 A1 | 11/2007 | Lindemann et al. |
| 2007/0282337 A1 | 12/2007 | Garamszegi |
| 2008/0077134 A1 | 3/2008 | Dziedzic et al. |
| 2008/0077135 A1 | 3/2008 | Stad et al. |
| 2008/0243190 A1 | 10/2008 | Dziedzic et al. |
| 2008/0255574 A1 | 10/2008 | Dye |
| 2009/0030419 A1 | 1/2009 | Runco et al. |

(56) References Cited

U.S. PATENT DOCUMENTS

| | | |
|---|---|---|
| 2009/0030420 A1 | 1/2009 | Runco et al. |
| 2009/0054902 A1 | 2/2009 | Mickiewicz et al. |
| 2009/0082811 A1 | 3/2009 | Stad et al. |
| 2009/0088764 A1 | 4/2009 | Stad et al. |
| 2009/0138056 A1 | 5/2009 | Anderson et al. |
| 2009/0143828 A1 | 6/2009 | Stad et al. |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0093022 A1 | 4/2011 | Runco et al. |
| 2012/0253413 A1 | 10/2012 | Runco et al. |

FOREIGN PATENT DOCUMENTS

| | | |
|---|---|---|
| EP | 948939 A2 | 10/1999 |
| EP | 1574175 A1 | 9/2005 |
| EP | 1648320 A2 | 4/2006 |
| EP | 1796564 A1 | 6/2007 |
| FR | 2677242 A1 | 12/1992 |
| FR | 2680314 A1 | 2/1993 |
| FR | 2729291 A1 | 7/1996 |
| WO | WO-9621396 A1 | 7/1996 |
| WO | WO-2005006948 A2 | 1/2005 |
| WO | WO-2006020443 A1 | 2/2006 |

OTHER PUBLICATIONS

International Search Report and Written Opinion mailed Nov. 6, 2008 for Application No. PCT/US2008/072851.

International Search Report (PCT/US2008/068515) dated Jan. 2, 2009.

U.S. Patent No. 6,790,209 Reissue Application Declaration and related Transmittal Letter and Information Disclosure Statement citing schematic drawings from Sofamor, "Introducteur—Contreur De Tige", Jan. 1, 1994.

* cited by examiner

FIG. 6A
FIG. 6B
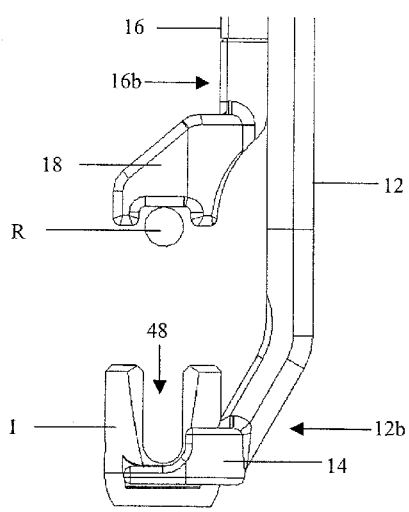
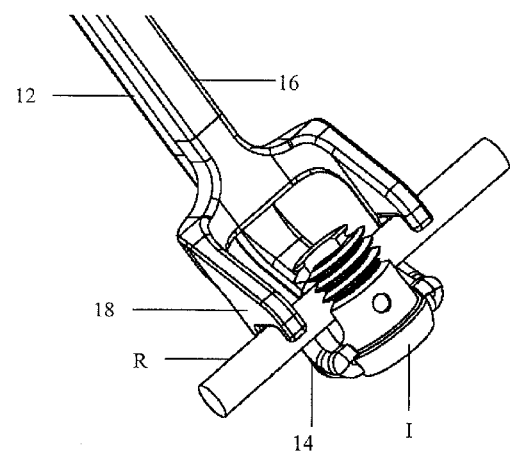

SPINAL ROD APPROXIMATOR

CROSS-REFERENCE TO RELATED APPLICATIONS

This application is a continuation of U.S. application Ser. No. 10/352,687 filed on Jan. 28, 2003 and entitled "Spinal Rod Approximator," which is hereby incorporated by reference in its entirety.

FIELD OF THE INVENTION

The present invention relates to spinal fixation systems, and in particular to a spinal rod approximator, a spinal implant, and methods for using the same.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism, is used to lock the fixation rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of locking mechanism to securely interconnect each screw and the fixation rod.

While current spinal fixation systems have proven effective, difficulties have been encountered in mounting rods into the rod-receiving portion of various fixation devices. In particular, it can be difficult to align and seat the rod into the rod receiving portion of adjacent fixation devices due to the positioning and rigidity of the vertebra into which the fixation device is mounted. Thus, the use of a spinal rod approximator, also referred to as a spinal rod reducer, is often required in order to grasp the head of the fixation device, and reduce the rod into the rod-receiving portion of the fixation device.

While several rod approximators are known in the art, some tend to be difficult and very time-consuming to use. Accordingly, there is a need for an improved rod approximator, implants for use with rod approximators, and methods for seating a spinal rod in a rod-receiving portion of one or more spinal implants.

SUMMARY OF THE INVENTION

The present invention provides medical devices and methods for seating a stabilizing rod in a rod-receiving portion of a spinal implant, and spinal implants for use with a rod approximator. In one embodiment, a rod approximator device is provided including an elongate member having a proximal end and a distal end defining an axis extending therebetween, and a grasping member extending from the distal end of the elongate member in a direction substantially transverse to the axis. The grasping member is effective to engage a spinal implant, and can optionally define opposed arms adapted to slide into and engage corresponding slots formed in a spinal implant. The device further includes a rod pusher member slidably mated to the elongate member and movable along the axis between a first position in which the rod pusher member is positioned a distance apart from the grasping member and is effective to grasp a stabilizing rod, and a second position in which the rod pusher member is positioned adjacent to the grasping member and is effective to position the grasped stabilizing rod in a rod-receiving portion of a spinal implant being engaged by the grasping member.

The rod approximator device of the present invention can also include an actuating member that can be coupled to the proximal end of the elongate member and the rod pusher member. The actuating member is effective to move the rod pusher member with respect to the grasping member. The actuating member can have a variety of configurations and in one embodiment it comprises opposed first and second members. A force applied to bring the first and second members toward one another is effective to move the rod pusher member from the first position to the second position. The actuating member can extend in a direction substantially transverse to the axis of the elongate member, and can optionally extend in a direction opposed to the grasping member. In an exemplary embodiment, the actuating member is in the form of a handle or grip and it comprises a first, stationary member mated to the proximal end of the shaft, and a second, opposed movable member linked to the proximal end of the elongate member. A force applied to bring the second, movable member toward the first, stationary member is effective to move the rod-engaging member from the first position to the second position. The actuating member can optionally include a ratchet mechanism effective to move the rod pusher member from the first position to the second position in predetermined increments. A release mechanism can be coupled to the ratchet mechanism to release the ratchet mechanism to enable the rod pusher member to return to the first position. The device can also optionally include a locking mechanism effective to lock the actuating member in one of the first or second positions, or optionally in an intermediate position between the first and second positions.

The rod pusher member of the approximator device can also have a variety of configurations. In one embodiment, the rod pusher member can include a shaft having proximal and distal ends, and can be slidably mounted on the elongate member along the axis. The rod pusher member can also include a rod-engaging member mated to the distal end of the shaft and preferably offset a distance apart from the shaft in a direction substantially transverse to the axis. The rod-engaging member can have a substantially semi-cylindrical shape and can include at least one rod-engaging recess formed on a distal facing portion thereof. In an exemplary embodiment, the grasping member defines opposed arms adapted to slide into and engage corresponding slots formed in a spinal implant, and at least one rod-engaging recess is formed in the rod-engaging member and is axially aligned with the opposed arms of the grasping member.

In another embodiment of the present invention, a system for seating a stabilizing rod in a rod-receiving portion of a spinal implant is provided. The system includes a spinal implant having a distal, bone engaging portion, and a proximal head including a base portion mated to the distal, bone engaging portion. A rod-receiving recess is formed in the proximal head for seating a stabilizing rod. The system further includes a rod reduction device having an elongate member with a distal grasping member formed thereon and offset from a longitudinal axis of the elongate member. The grasping member is adapted to engage and grasp the base portion of the head of the spinal implant. The rod reduction device also includes a rod pusher member slidably mounted on the elongate member and effective to grasp a stabilizing rod and, upon actuating, to push the rod into the rod-receiving recess formed in the spinal implant.

In an exemplary embodiment, the distal grasping member is substantially U-shaped, and the base portion of the head of the implant includes opposed slots formed therein. Preferably, the grasping member is adapted to slide into the slots on the implant to grip the implant. The opposed slots formed in the base portion of the head of the spinal implant can have a variety of configurations. In one embodiment, the slots each include an upper and lower shoulder. The lower shoulder is preferably substantially planar, and the upper shoulder is preferably substantially planar and includes opposed ends that are curved in a direction away from the lower shoulder. In other aspects of the invention, the head of the spinal implant can have a substantially hollow, cylindrical shape and can include opposed cut-out portions that form the rod-receiving recess for seating a stabilizing rod. The opposed slots formed in the base portion of the head of the spinal implant are preferably positioned distally adjacent to the opposed cut-out portions formed in the head of the spinal implant.

In yet another embodiment, the rod pusher member comprises an elongate shaft having proximal and distal ends that extend along the longitudinal axis, and a rod-engaging member mated to the distal end of the shaft and offset a distance apart from the axis of the shaft. An actuating member can be mated to the elongate member and the rod pusher member, and is effective to selectively move the rod pusher member between a first position in which the rod-engaging member is offset a distance apart from the grasping member, and a second position in which the rod-engaging member is positioned adjacent to the grasping member and is effective to position a stabilizing rod in the rod-receiving recess formed in the head of the spinal implant that is being engaged by the grasping member. In a preferred embodiment, the actuating member extends in a direction substantially transverse to the axis, and more preferably, the actuating member extends in a direction opposed to the grasping member.

In yet another embodiment of the present invention, a spinal implant is provided having a substantially hollow, cylindrical shaped head member including an open, proximal end and a closed, distal end. A bone-engaging member extends from the closed, distal end of the head member and is effective to engage bone. The head member includes a rod-receiving recess formed from opposed cut-out portions extending from the open, proximal end and terminating proximal to the closed, distal end. The head further includes opposed slots formed in a base of the head proximal to the closed, distal end and distal to the cut-out portions. The opposed slots are effective to receive opposed arms of a rod reduction device to enable the rod reduction device to engage the head of the spinal implant and to engage a stabilizing rod to push the rod into the rod-receiving recess formed in the head of the spinal implant.

The opposed slots formed in the base portion of the head of the spinal implant can each include an upper and lower shoulder. The lower shoulder is preferably substantially planar, and the upper shoulder is preferably substantially planar and includes opposed ends that are curved in a direction away from the lower shoulder.

Methods for reducing a stabilizing rod into a rod-receiving portion of a spinal implant are also provided.

BRIEF DESCRIPTION OF THE DRAWINGS

The invention will be more fully understood from the following detailed description taken in conjunction with the accompanying drawings, in which:

FIG. 6A is a side view illustration of the distal portion of a rod approximator device in a non-actuated position;

FIG. 6B is a side view illustration of the distal portion of the rod approximator device shown in FIG. 6A in the actuated position;

DETAILED DESCRIPTION OF THE INVENTION

In general, the present invention provides spinal fixation systems, and in particular a spinal implant, a spinal rod approximator for seating a stabilizing rod in a rod-receiving portion of a spinal implant, and methods for using the same. The spinal implants and spinal rod approximators of the present invention are particularly effective in that they are easy to use, they do not require significant force to operate, and they are efficient, thereby reducing the time and expense necessary to perform spinal surgery.

Figure 1:
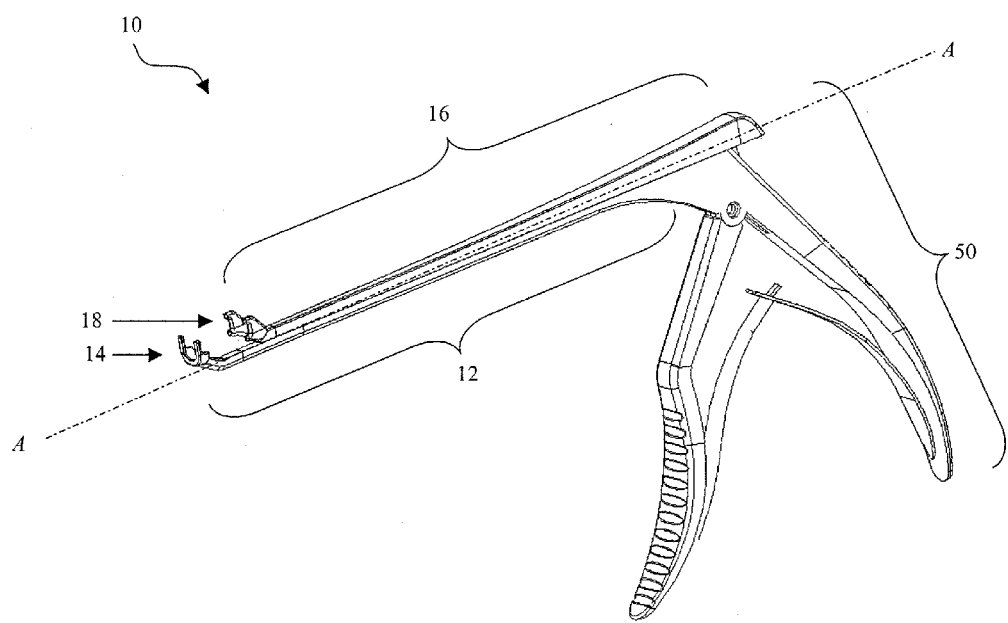
FIG. 1 is perspective view illustration of a spinal rod approximator according to one embodiment of the present invention.

FIG. 1 illustrates one embodiment of a spinal rod approximator 10 that is effective to engage and seat a stabilizing rod in a rod-receiving portion of a spinal implant. As shown, the tool 10 generally includes an elongate member 12 having a grasping member 14 formed on a distal end thereof, and a rod pusher member 16 slidably mated to or mounted on the elongate member 12. The grasping member 14 is effective to grasp a portion of a spinal implant, and the pusher member 16 is effective to grasp and engage a stabilizing rod and push the rod into a rod-receiving portion of the spinal implant being grasped by the grasping member 14.

A person having ordinary skill in the art will appreciate that while the tools and devices illustrated herein are described for use with spinal surgery, the tools can be adapted for use with a variety of medical procedures.

Figure 2:
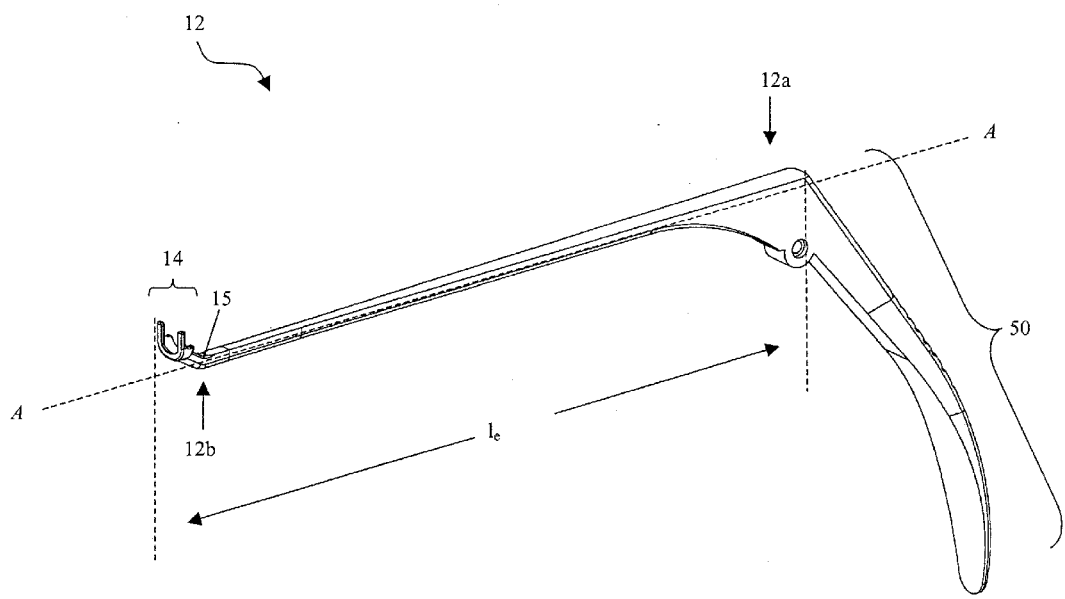
FIG. 2 is a perspective view illustration of the grasping member of the device shown in FIG. 1.

The elongate member 12 of the rod approximator 10 is shown in more detail in FIG. 2. The elongate member 12 can have a variety of shapes and sizes, but is preferably a generally elongate, solid rigid member having a proximal end 12a and a distal end 12b. The cross-sectional shape and size of the elongate member 12, as well as the length $1_e$ of the elongate member 12, can vary depending on the intended use. The elongate member 12 should, however, be substantially rigid to prevent bending thereof, and should have a length $1_e$ sufficient to enable the distal end 12b of the elongate member 12 to be placed adjacent to a surgical site while the proximal end 12a of the elongate member 12 remains outside a patient's body. By varying the size and shape, the elongate member 12 can also be adapted for use in minimally invasive procedures. By way of non-limiting example, the elongate member 12 can be configured to be disposed through an access tube or similar device.

Figure 3A:
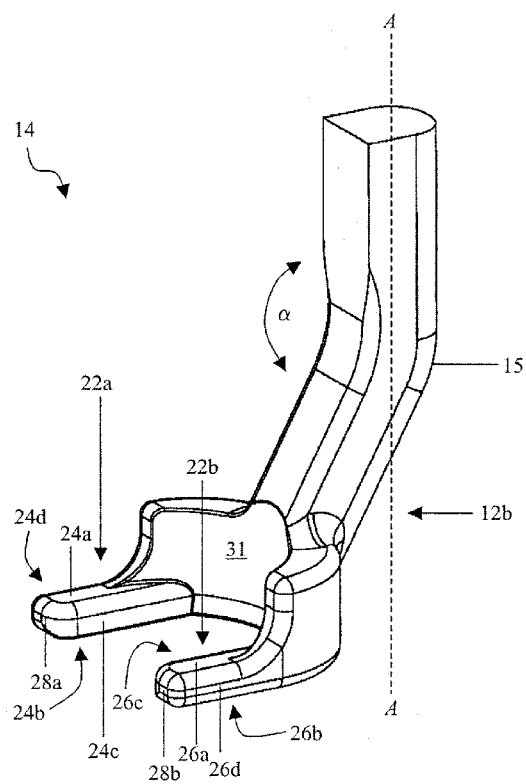
FIG. 3A is a perspective view illustration of one embodiment of the grasping portion formed on the distal end of the grasping member shown in FIG. 2.
Figure 3B:
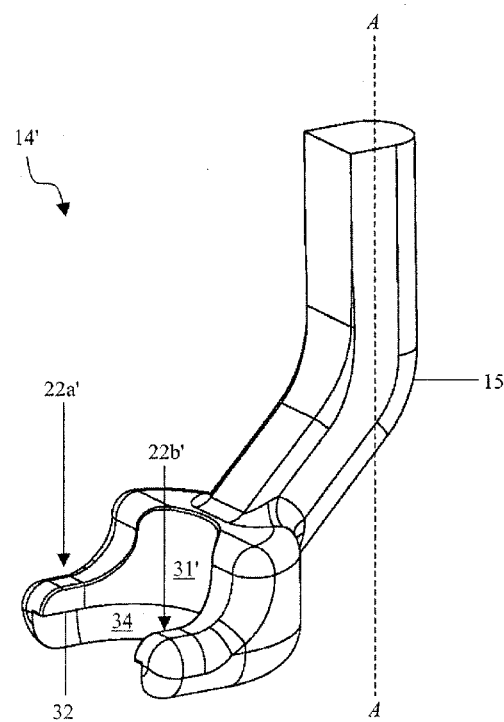
FIG. 3B is a perspective view illustration of another embodiment of the grasping portion formed on the distal end of the grasping member shown in FIG. 2.

The distal end 12b of the elongate member 12 includes a mating element 14 that is effective to grasp a spinal implant. The mating element 14 can have a variety of configurations, but is preferably a U-shaped grasping member 14 that is effective to grasp and engage a spinal implant. The grasping member 14 can be mated to the distal end 12a of the elongate member 12 using a variety of mating techniques, or it can be integrally formed thereon. Preferably, the grasping member 14 is integrally formed with the elongate member 12, and extends in a direction substantially transverse to an axis A of the elongate member 12. The grasping member 14 can also be positioned at a distance offset from the axis A of the elongate member 12 to facilitate use of the device. The offset position is particularly advantageous in that the implant can be grasped by the device while avoiding contact with adjacent bone structures. The offset position can be formed by providing a bend 15 in the distal end 12b of the elongate member 12, as shown in FIGS. 2-3B. While the angle α of the bent portion with respect to the axis A of the elongate member 12 can vary, the angle α is preferably in the range of about 15° to 60°, and more preferably is about 45° with respect to the axis A.

Still referring to FIGS. 3A and 3B, the grasping member 14 is adapted to mate with corresponding mating elements formed on the head portion of a spinal implant, as will be discussed in more detail with respect to FIGS. 11A-11C. While the grasping member 14 can have a variety of configurations, FIG. 3A illustrates one embodiment of a grasping member 14 having opposed arms 22a, 22b that extend outward from a semi-cylindrical wall 31 in a direction substantially perpendicular to the axis A of the elongate member 12. The semi-cylindrical wall contoured to the head of an implant being engaged, and it is adapted to fit around and seat the head of the implant. Further, the arms 22a, 22b are configured to fit within corresponding recesses or slots formed in the head of the implant.

Each arm 22a, 22 can have virtually any shape and size, and the arms can include several different mating features to facilitate grasping of the implant. As shown, the opposed arms 22a, 22b have a generally elongate, rectangular shape and include opposed proximal and distal surfaces 24a, 24b, 26a, 26b, and opposed inner 24c, 26c and outer 24d, 26d side surfaces, respectively. The proximal and distal surfaces 24a, 24b, 26a, 26b, and opposed inner 24c, 26c and outer 24d, 26d side surfaces are each preferably substantially planar. The distal most end 28a, 28b of each arm 22a, 22b can be rounded to facilitate insertion of the arms 22a, 22b into the corresponding slots formed in the head of the implant, and to prevent any potential damage to tissue surrounding the treatment site. Each arm of the grasping member can also optionally include a curved and/or narrowed distal tip 28a, 28b. Preferably, the proximal surface 24a, 26a of each arm 22a, 22b is ramped such that the distal tip 28a, 28b of each arm has a width less than a width of the proximal portion of the arm 22a, 22b. The narrowed tip allows the arms to be inserted into corresponding slots formed in a spinal implant at a variety of angles, thereby facilitating use of the device.

FIG. 3B illustrates another embodiment of a grasping member 14' that includes an inner recess 32 formed thereon that is adapted to receive a corresponding ridge formed around a base portion of the spinal implant. As shown, the recess 32 is formed around the distal most portion of the inner surface of the grasping member 14', and extends around the inside of both arms 22a', 22b' and optionally can extend around the semi-cylindrical wall 31'. The inner wall 34 is preferably slightly concave so as to be contoured to the rounded shape of the head of the implant. In use, an annular ridge formed around the head of the spinal implant slides into the recess 32 and the inner wall 34 fits securely around the base portion of the implant to allow the grasping member 14' to engage the implant.

Figure 3C:
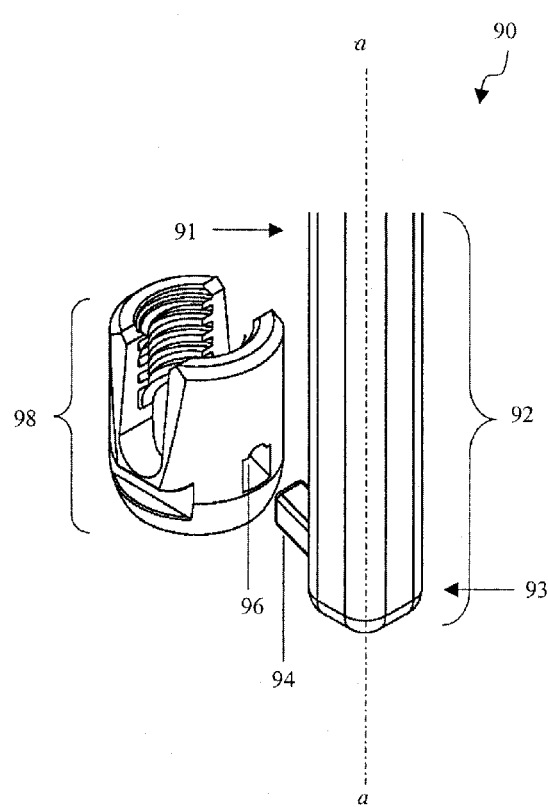
FIG. 3C is a perspective view illustration of yet another embodiment of a grasping portion of a grasping member according to the present invention.
Figure 3D:
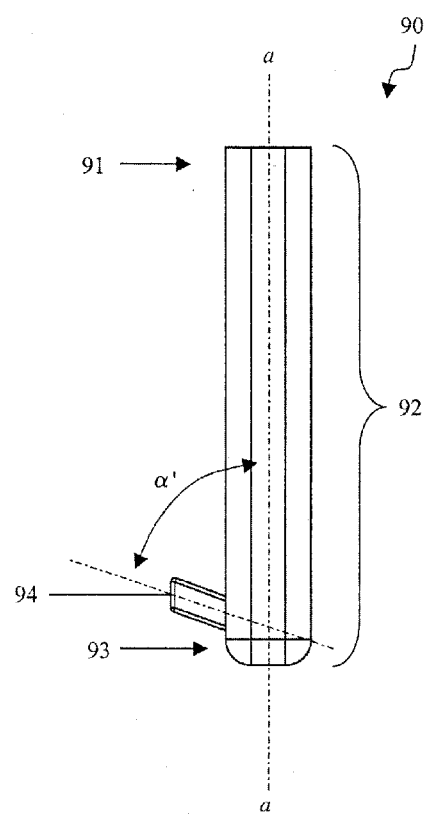
FIG. 3D is a side view illustration of the grasping portion shown in FIG. 3C.

FIGS. 3C-3D illustrate yet another embodiment of a grasping member 90 having a pin and bore connection. As shown, the distal end 93 of the elongate member 92 includes a pin 94 disposed thereon that extends in a direction transverse to the axis a. The pin 94 preferably extends toward the proximal end 91 of the elongate member 92 at an angle α' with respect to the axis a, and has a shape and size adapted to fit within a corresponding bore 96 formed in the head 98 of the implant. The pin 94 and the bore 96 can have virtually any shape and size, but the pin 94 should be configured to securely grasp the head 98 of the implant when inserted in the bore 96. The angle α' of the pin 94 facilitates a secure engagement of the head 98 as the angle α' prevents the pin 94 from falling out of the bore 96 when a proximally-directed force is applied to the elongate member 92.

A person having ordinary skill in the art will appreciate that the grasping members 14, 14', 90 shown in FIGS. 3A-3C are not intended to limit the scope of the invention. The grasping member can significantly vary in shape and size, and can be, for example, square or oval. The term "U-shaped" is intended to include any grasping member that is effective to grasp and engage an implant, and is not limited to grasping members having a U-shape. The grasping member and/or the head of the spinal implant can also include a variety of mating elements, including tongue-and-groove connections, dovetail connections, etc. Alternatively, the grasping member can be formed from, for example, opposed pin-type members that are adapted to fit within corresponding bores formed in the head of an implant. The arms can also optionally be slightly flexible to allow the arms to snap-around a portion of the head of a spinal implant.

Figure 4:
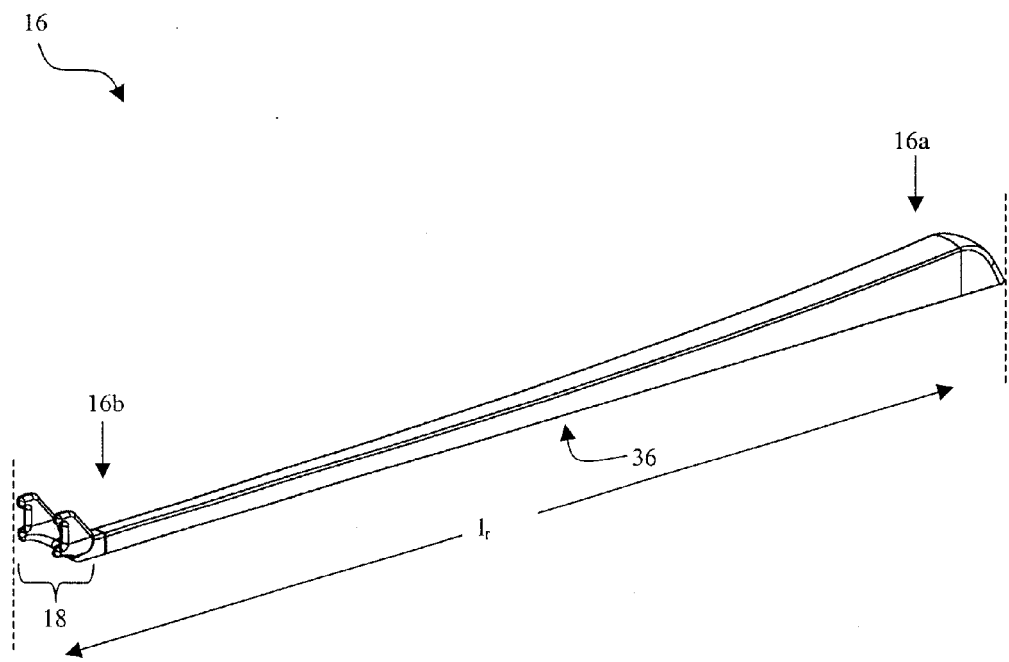
FIG. 4 is perspective view illustration of the rod pusher member of the device shown in FIG. 1.

FIG. 4 illustrates the rod pusher member 16 which is slidably mounted on and/or mated to the elongate member 12, and is effective to engage and push a spinal rod toward the grasping member 14 to seat the rod in a rod-receiving portion of an implant being engaged by the grasping member 14. The rod pusher member 16 can also have a variety of configurations, but is preferably a generally elongate rigid member having a proximal end 16a and a distal end 16b. The size and cross-sectional shape of the rod-pusher member 16 can vary, but preferably the rod-pusher member 16 has a generally cross-sectional shape and includes a substantially planar mounting surface 36 adapted to rest on the elongate member 12. The length $1_r$ of the rod pusher member 16 can also vary, but preferably the rod pusher member 16 has a length $1_r$ less than the length $1_e$ of the elongate member 12.

The rod pusher member 16 can be mated to the elongate member 12 using a variety of mating techniques. By way of non-limiting example, the rod pusher member 16 can include a channel or groove (not shown) formed therein, and the elongate member 12 can include a corresponding tongue (not shown) formed thereon and adapted to be slidably disposed within the groove. A person having ordinary skill in the art will appreciate that virtually any mating technique can be used to slidably mate the rod pusher member 16 to the elongate member 12.

The distal end 16b of the rod pusher member 16 is adapted to engage a spinal fixation rod, and thus can include a rod-engaging member 18 formed thereon. The rod-engaging member 18 can have a variety of configurations, and can be positioned adjacent to the grasping member 14, or can be offset from the grasping member 14. The rod-engaging member 18 can be integrally formed on the distal end 16b of the rod pusher member 16, or alternatively it can be removably mated to the rod pusher member 16. The rod-engaging member 18 can also optionally be adjustably mounted onto the rod pusher member 16 to allow the length $1_r$ of the rod pusher member 16 to be adapted based on the intended use of the device.

Figure 5:
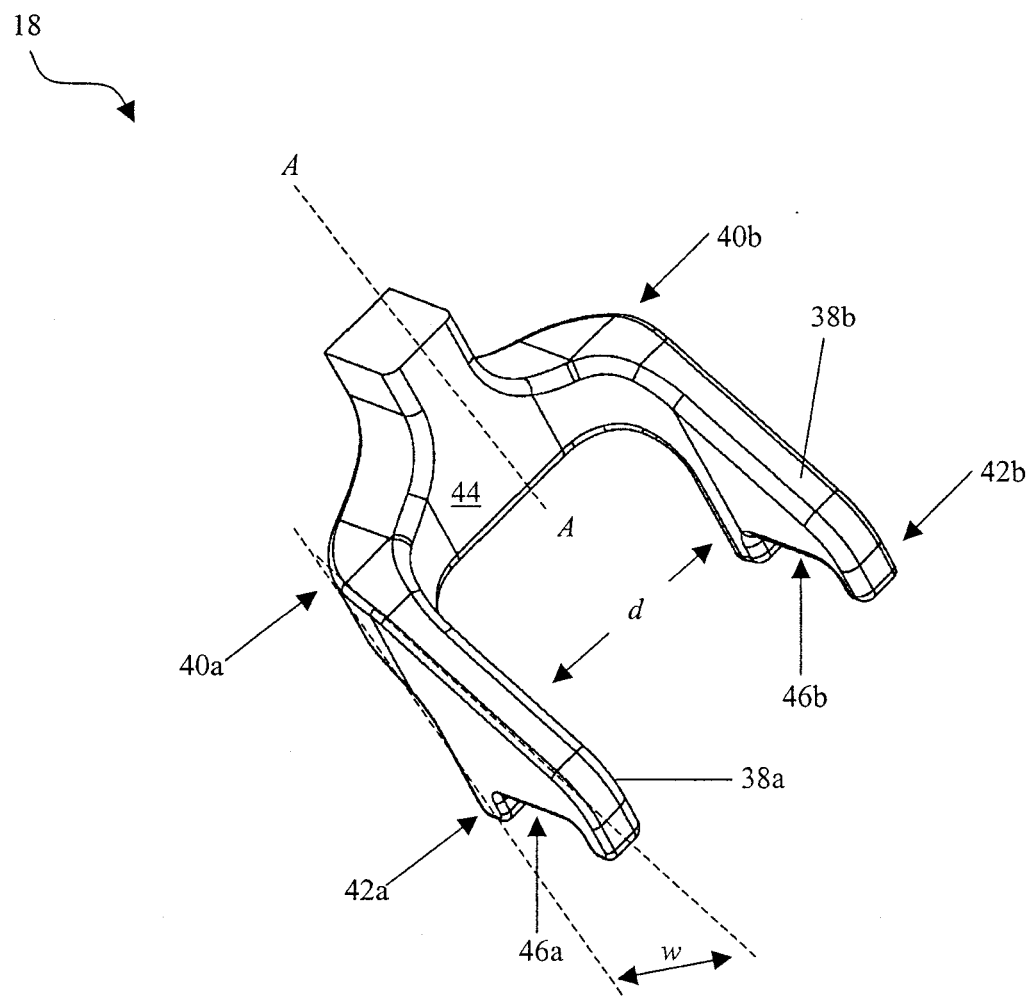
FIG. 5 is a perspective view illustration of one embodiment of the rod-engaging portion formed on the distal end of the rod pushing member shown in FIG. 4.

FIG. 5 illustrates one embodiment of a rod-engaging member 18 having opposed arms 38a, 38b that are adapted to engage and push a rod toward the grasping member 14. The arms 38a, 38b are preferably mated to a T-shaped member 44 formed on the distal end 16b of the rod pusher member 16, and each arm 38a, 38b is preferably positioned a distance d apart from one another to allow the arms 38a, 38b to be positioned around the head of an implant, and to allow access to a rod-receiving portion formed in the head of the spinal implant being engaged by the grasping member 14. The arms 38a, 38b are each also preferably aligned with the arms 22a, 22b of the grasping member 14, and they preferably extend in a direction substantially perpendicular to the T-shaped member 44. The arms 38a, 38b and the T-shaped member 44 can have a substantially semi-cylindrical shape, or can have a variety of other shapes.

Each arm 38a, 38b itself can also vary in shape and size, but preferably each arm is substantially planar and has a generally ramp-like shape such that width w of each arm 38a, 38b, extending in a direction transverse to the axis A, increases from the proximal end 40a, 40b to the distal, rod-engaging end 42a, 42b. The ramp-like shape of the arms 38a, 38b facilitates access to the rod-receiving portion of the spinal implant.

The distal, rod-engaging end 42a, 42b of each arm 38a, 38b can include a recess 46a, 46b formed therein for seating a stabilizing rod. The recesses 46a, 46b can have virtually any shape, such as square or semi-cylindrical. The recesses 46a, 46b can also be generally elongated to facilitate grasping of the stabilizing rod.

A person having ordinary skill in the art will appreciate that the rod pusher member can have a variety of configurations, but should be adapted to grasp and push a spinal fixation rod into a rod-receiving portion of a spinal implant.

In use, the rod pusher member 16 is movable between a first proximal position, shown in FIG. 6A, in which the distal end 16b of the rod pusher member 16 is positioned proximal to and a distance apart from the grasping member 14 formed on the distal end 12b of the elongate member 12, and a second position, shown in FIG. 6B, in which the distal end 16b of the rod pusher member 16 is positioned adjacent to, or is in contact with, the grasping member 14. In the first position, the rod pusher member 16 is effective to grasp a spinal fixation rod R. The rod pusher member 16 can then be moved to the second position to push the rod R into a rod receiving portion 48 of a spinal implant I being engaged by the grasping member 14.

In order to move the rod pusher member 16 between the first and second positions, the proximal end 12a of the elongate member 12 and the proximal end 16a of the rod pusher member 16 can be mated to an actuating member 50. The actuating member 50 can extend along the axis A of the device 10, but it preferably extends in a direction substantially transverse to the axis A. More preferably, the actuating member 50 can be a handle or grip-like element that extends in a direction opposed to the grasping member 14 and the rod engaging member 18. This configuration provides better visual access to the surgical site.

Figure 7:
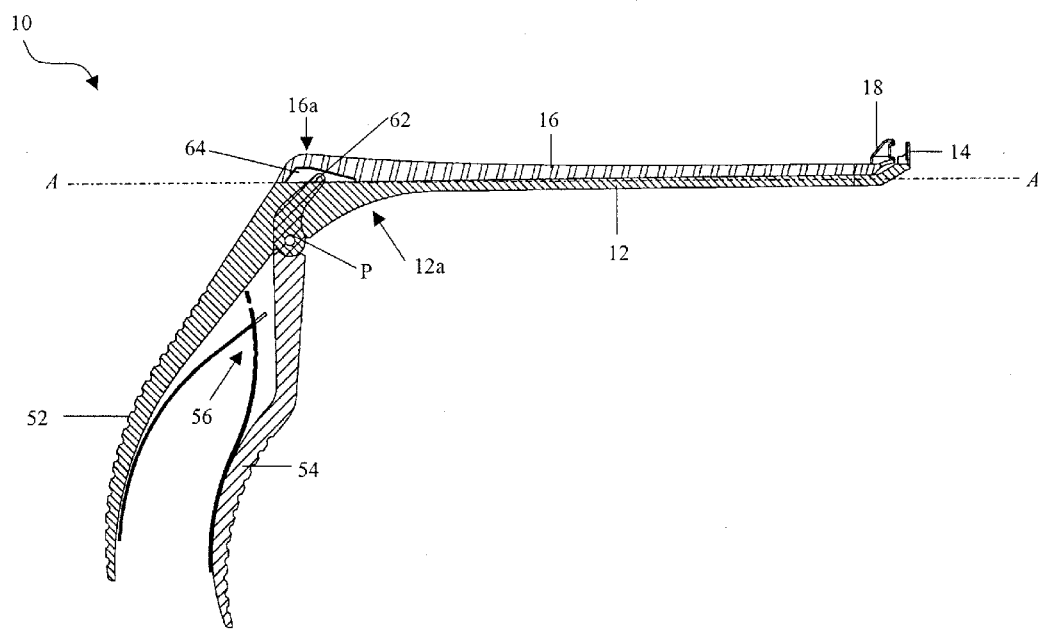
FIG. 7 is a sectional view illustration of the spinal rod approximator shown in FIG. 1 according to the present invention.

While virtually any actuating member can be used with the present invention, FIGS. 1 and 7 illustrate a preferred embodiment of an actuating member 50 having first and second opposed handle members 52, 54. The first handle member 52 is mated to or formed integrally with the proximal end 12a of the elongate member 12, and the second handle member 54 is linked to the proximal end 16a of the rod pusher member 16. Both of the handle members 52, 54 can be movably mated to one another, but preferably the first handle member 52 is stationary and fixedly attached to the elongate member 12, and the second handle member 54 is pivotally mated to the first handle member 52 and to the rod pusher member 16. As shown, the handle members 52, 54 are mated to one another at pivot point P. The second handle member 54 is adapted to rotate at pivot point P, and is mated to the rod pusher member 16 to move the rod pusher member 16 between the first and second positions. As shown, the second handle member 54 includes a distal end 62 that extends into a slot 64 formed in the rod pusher member 16. Movement of the handle 54 from the non-actuated position, shown in FIG. 1, to the actuated position, shown in FIG. 7, causes the distal end 62 of the handle 54 to engage the slot 64 and move the rod pusher member 16 in a distal direction. A person having ordinary skill in the art will appreciate that a variety of techniques can be used to effect movement of the rod pusher member 16.

The actuating member 50 can also optionally include a biasing element 56 disposed between the handle members 52, 54. The biasing element 56 is preferably effective to bias the first and second handle members 52, 54 to an open position, as shown in FIG. 1, wherein the rod-engaging member 18 is positioned a distance apart from the grasping member 14. A force can be applied to the first and second handle members 52, 54 to overcome the biasing force of the biasing element 56, and thereby move the rod pusher member 16 from the first, proximal position to the second, distal position. A variety of biasing elements 56 can be used with the actuating member 50 including, for example, spring mechanisms. As shown in FIGS. 1 and 7, the biasing element 56 is formed from opposed flexible members that force the first and second members into the open position.

A person having ordinary skill in the art will appreciate that virtually any actuating member can be used to move the rod-pusher member 16 and/or the elongate member 12 between the open and closed positions. By way of non-limiting example, the device 10 can include a ratchet-type mechanism having a trigger that, upon actuating, is effective to move the rod pusher member 16 in a distal direction in predetermined increments with respect to the elongate member 12. The device 10 can also optionally include a locking mechanism effective to lock the device 10 in the second, actuated position. A person having ordinary skill in the art will appreciate that the device can include a variety of other features to facilitate use of the device.

Figure 8:
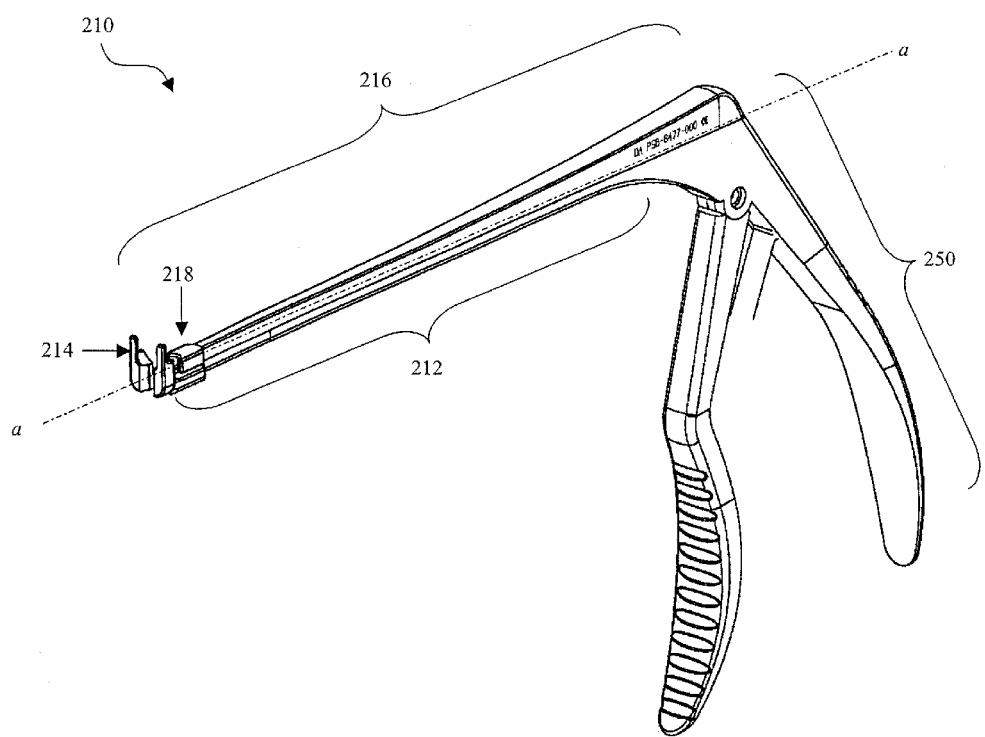
FIG. 8 is a perspective view illustration of another embodiment of a spinal rod approximator according to the present invention.
Figure 9:
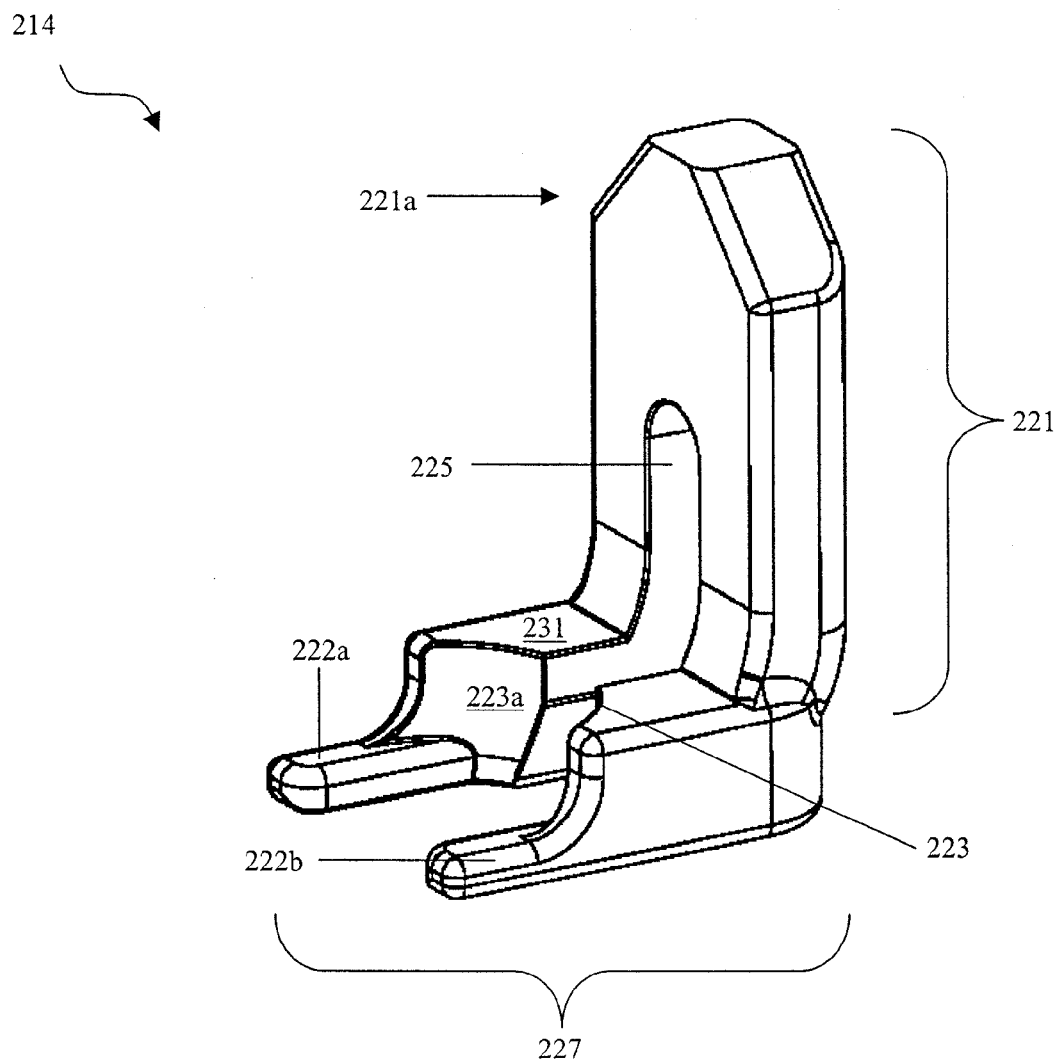
FIG. 9 is a perspective view illustration of the grasping member of the device shown in FIG. 8.
Figure 10:
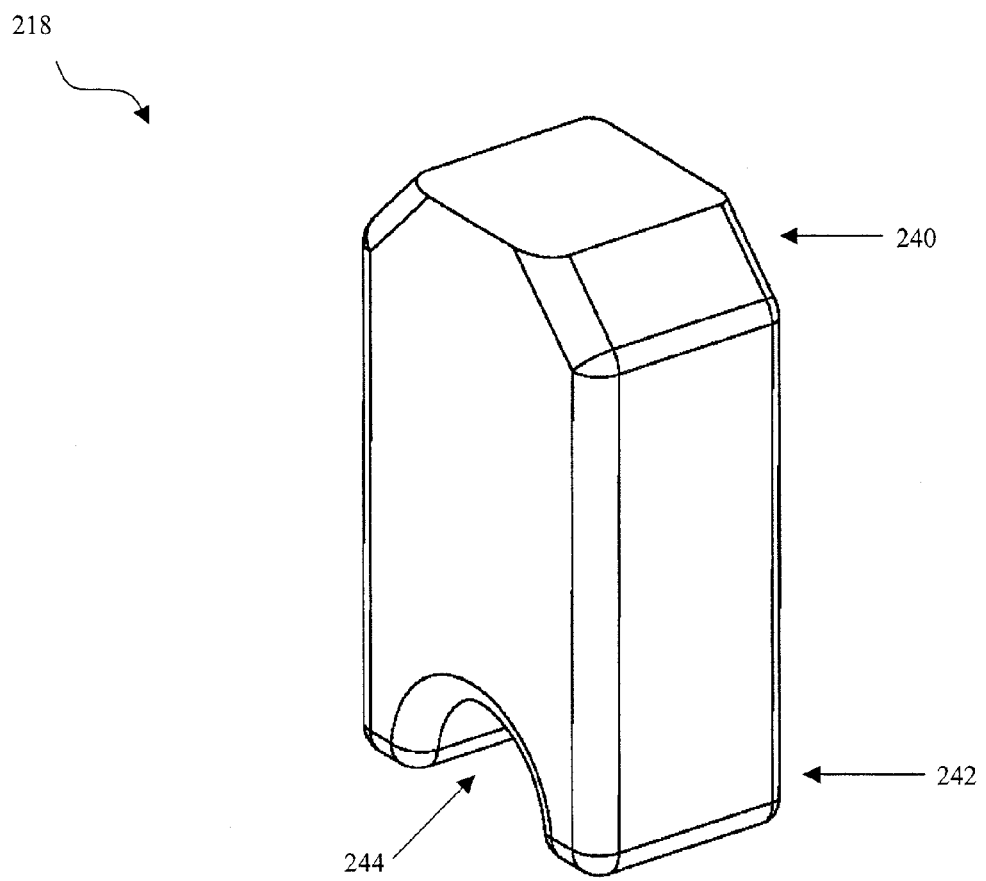
FIG. 10 is a perspective view illustration of one embodiment of the rod-engaging portion formed on the distal end of the rod pushing member shown in FIG. 8.

FIGS. 8-10 illustrate another embodiment of a spinal rod approximator 210 in which the rod reducer member 218 is substantially parallel to the axis a, rather than offset from the axis, as shown in FIG. 1 of rod reducer 10. Except as otherwise discussed herein, rod approximator 210 is substantially the same as rod approximator 10, and the elements of rod reducer 210 that are the same as the elements of rod reducer 10 are similarly designated but have a prefix "2" added to the reference numeral used for that element in the description of rod reducer 210. As shown in FIG. 8, rod reducer 210 includes an elongate member 212 having a grasping member 214 formed on a distal end thereof, and a rod pusher member 216 slidably mated to or mounted on the elongate member 212. The grasping member 214 is effective to grasp a portion of a spinal implant, and the pusher member 216 is effective to grasp and engage a stabilizing rod and push the rod into a rod-receiving portion of the spinal implant being grasped by the grasping member 214.

The grasping member 214 is shown in more detail in FIG. 9 and includes a first, upright portion 221 that extends along the longitudinal axis a of the device 210, and a second portion 227 having opposed arms 222a, 222b that extend in a direction substantially perpendicular to the upright portion 221. The upright portion 221 can have virtually any shape and size, but should include a rod-seating recess 225 formed therein that extends from a position distal to the proximal end 221a of the upright portion through the second portion 227 to define the opposed arms 222a, 222b. The recess 225 is adapted to receive a rod that extends between the arms 222a, 222b in a direction substantially parallel to the direction of the arms 222a, 222b.

The arms 222a, 222b are similar to arms 22a, 22b shown in FIG. 1. Each arm 222a, 222b includes a semi-cylindrical wall 223a, 223b formed on proximal end thereof for contouring the head of an implant being engaged. The aims 222a, 222b are configured to fit within corresponding recesses or slots formed in the head of the implant. The slots in the implant (not shown should be positioned in a distal portion of each leg of a U-shaped head of an implant. This configuration allows the rod to be aligned with the rod-receiving portion in the head of the implant.

The rod-engaging member 218 is shown in more detail FIG. 10, and is effective to push a spinal rod toward an implant being grasped by the grasping member 214. The rod-engaging member 218 can have a variety of configurations, but as shown has a generally rectangular shape and includes opposed proximal and distal ends 240, 242. The proximal end 240 is mated to or integrally formed on the distal end of the rod-pusher member 216, and the distal end 242 is adapted to receive a spinal rod. The distal end 242 preferably includes a recess 244 formed therein for seating the spinal rod to facilitate reduction of the rod toward the implant being engaged by the grasping member 214. The recess 244 should extend in the same direction as the arms 222a, 222b of the grasping member 214 to allow a rod to be positioned between the arms 222a, 222b and seated in the recess 244.

In use, the device 210 is operated in the same manner as device 10, except that the implant is grasped in a different direction. In particular, device 10 grasps the implant beneath the rod-receiving recess formed in the U-shaped head of an implant, while device 210 grasps the implant along each leg of the U-shaped head. A person having ordinary skill in the art will appreciate that modifications can be made to the rod approximator to allow an implant to be grasped at different locations and in different directions with respect to the U-shaped head.

Figure 11A:
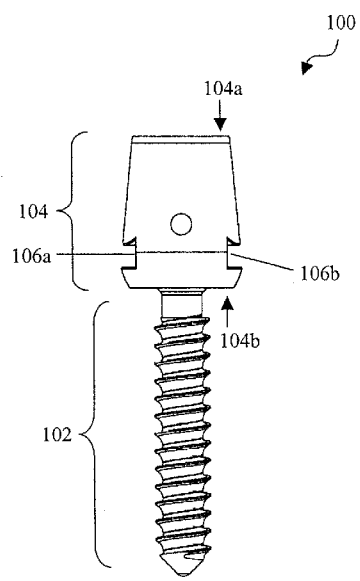
FIGS. 11A-11C are perspective view illustrations of a spinal implant according to one embodiment of the present invention.
Figure 11B:
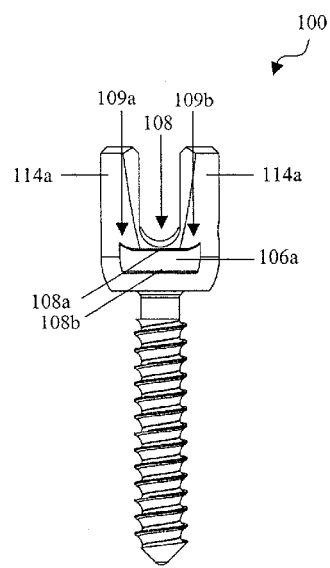
Figure 11C:
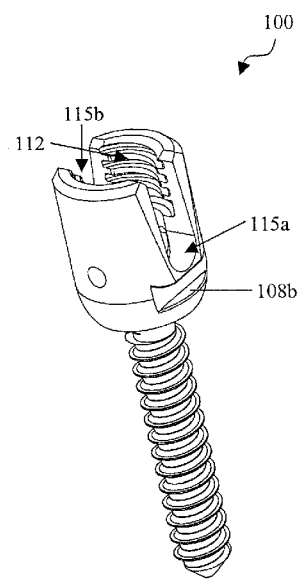

FIGS. 11A-11C illustrate one embodiment of a spinal implant 100 for use with a rod approximator according to the present invention. As shown, the implant 100 includes a threaded shank 102 and a generally U-shaped head 104 having an open proximal end 104a, and a closed distal end 104b attached to the shank 102. Preferably, the shank 102 is rotatably mated to the distal end 104b of the head 104 to allow rotation of the head 104. A variety of techniques can be used to allow rotation of the head with respect to the shank 102. By way of non-limiting example, the shank 102 can include an enlarged proximal portion (not shown) and can be disposed through a bore formed in the distal end 104b of the head 104. The enlarged proximal portion will prevent the shank 102 from extending completely through the bore. Once a spinal rod is disposed within the U-shaped head and secured by a closure mechanism, the rod will prevent rotation of the head 104 with respect to the shank 102.

The U-shaped head 104 includes opposed side walls 114a, 114b that define a rod-receiving portion 108 for seating a spinal fixation rod, and that are substantially parallel to one another. The inner surface of the head 104 includes threads 112 formed thereon for mating with a closure mechanism effective to secure the rod in the rod-receiving portion 108 of the head 104, and the outer surface of the head 104 includes opposed recesses 106a, 106b formed therein for receiving the arms 22a, 22b of the grasping member 14. The recesses 106a, 106b extend in a direction transverse to the direction of the side walls 114a, 114b, and are preferably positioned just proximal to the distal end 104b of the head 104. Thus, the recesses 106a, 106b are positioned distally adjacent to the cut out portions 115a, 115b that form the rod-receiving portion 108 of the head 104 of the implant 100. The recesses 106a, 106b can, however, be disposed in the distal portion of each side wall 114a, 114b to allow the implant to be grasped in an opposed direction. The position of the recesses 106a, 106b is particularly advantageous in that it facilitates engagement of the implant 100 by a rod approximator since the grasping member 14 does not need to grasp the implant 100 underneath the head 104. The position of the recesses 106a, 106b also avoids potential contact with adjacent bone structures.

Each recess 106a, 106b can have a variety of shapes and sizes, but preferably the recesses 106a, 106b are elongated slots which form upper and lower shoulders 108a, 108b. The upper and lower shoulders 108a, 108b can each be substantially planar, but preferably the lower shoulder 108b is substantially planar and the upper shoulder 108a is substantially planar but includes opposed ends 109a, 109b that are curved such that they extend away from the lower shoulder 108b. The curved shape of the upper shoulder 108a allows the arms 22a, 22b of the grasping member 14 to be inserted into the recesses 106a, 106b at an angle.

A person having ordinary skill in the art will appreciate that the implant 100 can have a variety of configurations, and that the features illustrates can be used on a variety of implants, includes hooks and other fastener devices.

In use, one or more spinal implants 100 are screwed into vertebral bone structures. Typically, where two spinal implants 100 are fastened into adjacent vertebra, a spinal rod is inserted into the rod-receiving portion 108 of each implant. However, due to the alignment of the implants 100, it can be difficult to position the rod within each rod-receiving recess 108. Thus, a rod approximator device is necessary. The rod approximator device 10 is used by inserting the arms 22a, 22b of the grasping member 14 into the corresponding recesses 106a, 106b of the head 104 of the implant 100. With the rod pusher member 16 in the first, proximal position, the device can be manipulated to place the spinal rod between the rod engaging member 18 and the head 104 of the implant 100. The first and second handle members 52, 54 can then be grasped and squeezed together to cause the rod pusher member 16 to move to the second, distal position, thereby causing the rod engaging member 18 to grasp and push the stabilizing rod into the rod-receiving recess 108 formed in the head 104 of the spinal implant 100. While maintaining the device 10 in the second, actuated position, a closure mechanism can be threaded into the head 104 of the spinal implant 100 to secure the stabilizing rod in the rod-receiving recess 108.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal implant, comprising:
a head member having a substantially hollow cylindrical shape with proximal and distal ends, the head member having a rod-receiving recess formed from opposed cut-out portions extending from the proximal end and terminating proximal to the distal end, and the head member having first and second slots formed therein on opposed sides of an outer surface of the head member, each of the first and second slots having a proximal upper shoulder and a distal lower shoulder, the upper shoulder having a curved shape such that opposed ends of the lower shoulder curve away from the lower shoulder such that the opposed ends of the upper shoulder are closer to the proximal end of the head member than a central portion of the upper shoulder to allow a grasping member of a rod reduction device to be inserted into the respective slots at an angle; and
a bone-engaging member extending from the distal end of the head member and effective to engage bone.

2. The implant of claim 1, further comprising first and second bore holes formed in opposed sides of the outer surface of the head member.

3. The implant of claim 2, wherein the first and second bore holes are spaced a distance apart from the proximal and distal ends of the head members.

4. The implant of claim 2, wherein the first and second bore holes are spaced a distance apart from the first and second slots.

5. The implant of claim 1, wherein the lower shoulder of the first and second slots is substantially planar.

6. The implant of claim 1, wherein the first and second slots each extend along a sidewall and each slot is situated distal of each cut-out in each sidewall containing the cut-out, such that the lower shoulder of each slot is closer to a distal end of the head member.

7. A spinal implant, comprising:
a rod-receiving head having proximal and distal ends, opposed cut-outs formed therein and extending distally from the proximal end for receiving a spinal fixation rod, opposed sidewalls extending between the opposed cut-outs, the sidewalk having threads formed on an inner surface thereof, first and second elongate slots formed in an outer surface of the head, disposed distal of the opposed cut-outs and extending between the two sidewalls, and positioned on opposed sides of the head, and first and second bore holes formed in opposed outer surfaces of the opposed sidewalls, respectively, such that the bores are positioned on opposed sides of the head, the first and second elongate slots and the first and second bore holes being spaced a distance apart from one another and being spaced a distance apart from the proximal and distal ends of the rod-receiving head; and
a bone-engaging member extending distally from the distal end of the rod-receiving head and configured to engage bone.

8. The implant of claim 7, wherein the first and second elongate slots each include an upper shoulder and a lower shoulder, and wherein the lower shoulder is substantially planar and the upper shoulder has a substantially curved shape such that opposed ends of the upper shoulder curve in a direction away from the lower shoulder.

9. The implant of claim 7, wherein the first and second elongate slots each extend along a side wall and each slot is situated distal of each cut-out in each sidewall containing the respective cut-out, such that a lower shoulder of each slot is closer to a distal end of the head member.

10. A system for seating a stabilizing rod in a rod-receiving portion of a spinal implant, comprising:
a spinal implant having a distal bone engaging portion and a proximal head having a rod-receiving recess formed therein for seating a stabilizing rod, the proximal head including first and second slots formed therein on opposed sides of the proximal head, the first and second slots having a substantially planar proximal upper shoulder and a substantially planar distal lower shoulder, the upper shoulder having first and second opposed ends, the upper shoulder curving away from the lower shoulder such that the first and second opposed ends are closer to a proximal end of the proximal head than a central portion of the upper shoulder; and
a rod reduction device having an elongate member with a distal portion configured to engage the first and second slots formed in the proximal end, and a rod pusher member movably coupled to the elongate member and effective to advance a stabilizing rod into the rod-receiving recess formed in the spinal implant.

11. The system of claim 10, wherein the lower shoulder is substantially planar.

12. The system of claim 10, further comprising an actuating member coupled to the elongate member and the rod pusher member, the actuating member being effective to selectively move the rod pusher member relative to the elongate member for advancing a stabilizing rod into the rod-receiving recess formed in the spinal implant.

13. A spinal implant, comprising:
a head member having a substantially hollow, cylindrical shape and including an open proximal end and a closed distal end with a longitudinal axis extending between the open proximal end and the closed distal end, and a rod-receiving recess formed from opposed cut-out portions extending from the open proximal end and terminating at a closed distal end that is proximal to the closed distal end of the head member, the head member further including opposed slots, each slot formed in the base of the head member at a location that is distal to the closed distal end of the respective cut-out portion and proximal to the closed distal end of the head member along said longitudinal axis, the opposed slots being effective to receive opposed arms of a rod reduction device to enable the rod reduction device to engage the head member of the spinal implant and to engage a stabilizing rod to push the rod into the rod-receiving recess formed in the head member of the spinal implant; and a bone-engaging member extending from the closed distal end of the head member and effective to engage bone.

14. The spinal implant of claim 13, wherein the opposed slots formed in the base portion of the head member of the spinal implant each include an upper and lower shoulder, and wherein the lower shoulder is substantially planar, and the upper shoulder is substantially planar and includes opposed ends that are curved in a direction away from the lower shoulder such that the opposed ends are more proximal to the proximal end of the head member than a central portion of the upper shoulder.

15. The implant of claim 13, wherein the opposed slots each extend along a sidewall and each slot is situated distal of each cut-out in each sidewall containing the respective cut-out, such that the lower shoulder of each slot is closer to a distal end of the head member.

* * * * *